US009999859B2

(12) United States Patent
Chen et al.

(10) Patent No.: US 9,999,859 B2
(45) Date of Patent: Jun. 19, 2018

(54) IMMOBILIZED MULTI-LAYER ARTIFICIAL MEMBRANE FOR PERMEABILITY MEASUREMENTS (PAMPA)

(71) Applicant: CORNING INCORPORATED, Corning, NY (US)

(72) Inventors: Xiaoxi (Kevin) Chen, Natick, MA (US); Charles L. Crespi, Marblehead, MA (US)

(73) Assignee: Corning Incorporated, Corning, NY (US)

( * ) Notice: Subject to any disclaimer, the term of this patent is extended or adjusted under 35 U.S.C. 154(b) by 0 days. days.

(21) Appl. No.: 14/613,774

(22) Filed: Feb. 4, 2015

(65) Prior Publication Data

US 2015/0144552 A1   May 28, 2015

Related U.S. Application Data

(62) Division of application No. 11/552,606, filed on Oct. 25, 2006, now Pat. No. 8,986,781.

(Continued)

(51) Int. Cl.
*B01D 69/14* (2006.01)
*G01N 15/08* (2006.01)
(Continued)

(52) U.S. Cl.
CPC .......... *B01D 69/144* (2013.01); *B01D 61/38* (2013.01); *B01D 67/0002* (2013.01);
(Continued)

(58) Field of Classification Search
CPC .. B01D 69/144; B01D 69/142; B01D 69/141; B01D 69/14; B01D 71/34; B01D 71/74;
(Continued)

(56) References Cited

U.S. PATENT DOCUMENTS 4,626,532 A * 12/1986 Kjellberg ............. A61K 9/1617
514/195
4,892,538 A * 1/1990 Aebischer ............... A61F 2/022
128/898

(Continued)

OTHER PUBLICATIONS

Di, Li, et al. "High throughput artificial membrane permeability assay for blood-brain barrier." European journal of medicinal chemistry 38.3 (2003): 223-232.*

(Continued)

*Primary Examiner* — David C Mellon
*Assistant Examiner* — Liam Royce
(74) *Attorney, Agent, or Firm* — Susan S. Wilks

(57) ABSTRACT

With the subject invention, a method is provided for preparing a filter membrane including the steps of dispersing a liquid which is generally hydrophobic into the pores of a porous membrane, and applying a solution containing lipids onto at least a first surface of the porous membrane containing the liquid. Advantageously, the subject invention allows for filter membranes to be prepared which can be stored for periods of time without degradation in performance. The subject invention may have applicability in various contexts, but is well-suited for preparing filter membranes for permeability screening, particularly Parallel Artificial Membrane Permeability Assay (PAMPA).

35 Claims, 10 Drawing Sheets

Related U.S. Application Data

(60) Provisional application No. 60/730,570, filed on Oct. 27, 2005.

(51) Int. Cl.
| | |
|---|---|
| *B01D 71/50* | (2006.01) |
| *B01D 71/34* | (2006.01) |
| *B01D 71/82* | (2006.01) |
| *B01D 71/74* | (2006.01) |
| *B01D 67/00* | (2006.01) |
| *B01D 69/10* | (2006.01) |
| *B01D 61/38* | (2006.01) |
| *G01N 1/40* | (2006.01) |
| *B01L 3/00* | (2006.01) |

(52) U.S. Cl.
CPC ............ *B01D 69/10* (2013.01); *B01D 71/34* (2013.01); *B01D 71/50* (2013.01); *B01D 71/74* (2013.01); *B01D 71/82* (2013.01); *G01N 15/08* (2013.01); *G01N 15/082* (2013.01); *B01D 2323/04* (2013.01); *B01L 3/50255* (2013.01); *G01N 2001/4016* (2013.01); *G01N 2015/084* (2013.01); *G01N 2015/086* (2013.01); *Y10T 436/255* (2015.01)

(58) Field of Classification Search
CPC ........ B01D 71/50; B01D 71/82; B01D 71/76; B01D 71/06; B01D 67/0002; B01D 69/10; B01D 61/38; B01D 2323/04; G01N 15/08; G01N 15/082; G01N 2001/4016; G01N 2001/4005; G01N 2001/40; G01N 2015/086; G01N 2015/08; G01N 2015/084; B01L 3/50255; B01L 3/5025; B01L 3/502; B01L 3/50; Y10T 436/255

See application file for complete search history.

(56) References Cited

U.S. PATENT DOCUMENTS

| | | | | |
|---|---|---|---|---|
| 5,177,064 | A * | 1/1993 | Bodor | A61K 47/48023 514/49 |
| 5,496,581 | A * | 3/1996 | Yianni | A61L 29/085 427/2.12 |
| 6,861,260 | B2 | 3/2005 | Sugano | |
| 6,863,833 | B1 * | 3/2005 | Bloom | B81B 1/004 204/403.08 |
| 6,887,432 | B2 | 5/2005 | Kansey et al. | |
| 7,060,428 | B2 | 6/2006 | Di et al. | |
| 2002/0094992 | A1 * | 7/2002 | MacLean | A61K 31/437 514/303 |
| 2003/0219716 | A1 | 11/2003 | Avdeef et al. | |
| 2005/0106745 | A1 | 5/2005 | Wexler et al. | |
| 2006/0009805 | A1 * | 1/2006 | Jensen | A61K 9/0004 607/2 |
| 2007/0116733 | A1 * | 5/2007 | Graneli | G01N 33/5432 424/423 |
| 2010/0032296 | A1 * | 2/2010 | Pluskal | G01N 27/4473 204/601 |

OTHER PUBLICATIONS

Nielsen P.E., Avdeef A. 2004. PAMPA—a drug absorption in vitro model: 8. Apparent filter porosity and the unstirred water layer Euro. J. Pharm. Sci., 22:1, p. 33-41, ISSN 0928-0987, https://doi.org/10.1016/j.ejps.2004.02.003. (http://www.sciencedirect.com/science/article/pii/S0928098704000417).*

Tecan Double-Sink PAMPA Assay for Permeability Studies technical brochure 2009.*

Avdeef, et al., Drug Absorption In Vitro Model: Filter-Immobilized Artificial Membranes 2. Studies of the Permeability Properties of Lactones in Piper Methysticum Forst, European Journal of Pharmaceutical Sciences 14, 2001, pp. 271-280.

Kansy et al., "Physicochecmical High Throughput Screening: Parallel Artificial Membrane Permeation Assay in the Description of Passive Absorption Processes", Journal of Medicinal Chemistry, vol. 41, No. 7, 1998, pp. 1007-1010.

Kansy et al., "Advances in Screening for Membrane Permeability: High-Resolution PAMPA for Medicinal Chemists", Drug Discovery Today: Technologies, Elsevier, vol. 1, No. 4, Dec. 2004, pp. 349-355, XP004767937, ISSN 1740-6749.

Flaten et al., "Drug Permeability Across a Phospholipid Vesicle Based Barrier: A Novel Approach for Studying Passive Diffusion", European Journal of Pharmaceutical Sciences, Elsevier, Amsterdam, NL, vol. 27, No. 1, Jan. 2006, pp. 80-90, XP005185002, ISSN: 0928-0987.

Ruell et al., "A Simple PAMPA Filter for Passively Absorbed Compounds," Poster, ACS National Meeting, Boston, Aug. 2002.

Sugano et al., "High Throughput Prediction of Oral Absorption: Improvement of the Composition of the Lipid Solution Used in Parallel Artificial Membrane Permeation Assay", J. Biomolecular Screening, 2001, 6, pp. 189-196.

Sugano et al., "Predicition of Human Intestinal Permeability Using Artificial Membrane Permeability", International Journal of Pharmaceutics 257, pp. 245-251, 2003.

Wohnsland et al., "High-Throughput Permeability pH Profile and High-Throughput Alkane/Water log P with Artificial Membranes", J. Med. Chem., 2001; 44, pp. 923-930.

Montal et al, "Formation of bimolecular membranes from lipid monolayers and a study of their electrical properties"; Proc Natl Acad Sci USA Dec. 1972; 69(12): 3561-6.

Liu et al. "In Vitro Permeability of Poorly Aqueous Soluble Compounds Using Different Solubilizers in the PAMPA Assay with Liquid Chromatography / Mass Spectrometry Detection", Pharmaceutical Research, vol. 20, p. 1820 (2003).

Hanke et al., "Chapter 5: Methods for making planar lipid bilayers" in Planar Lipid Bilayers: Methods and Applications. Academic Press 2012, pp. 60-78.

Andrews et al. "Chapter 2.08: Engineering Biometric Membranes with Hydrogels" in Comprehensive Nanoscience and Technology; Academic Press, Oct. 29, 2010, pp. 213-225.

* cited by examiner

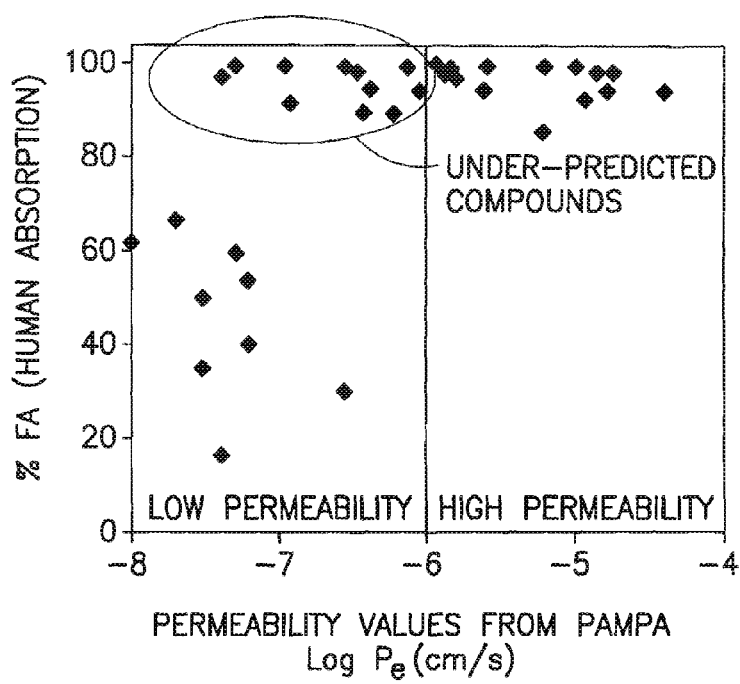
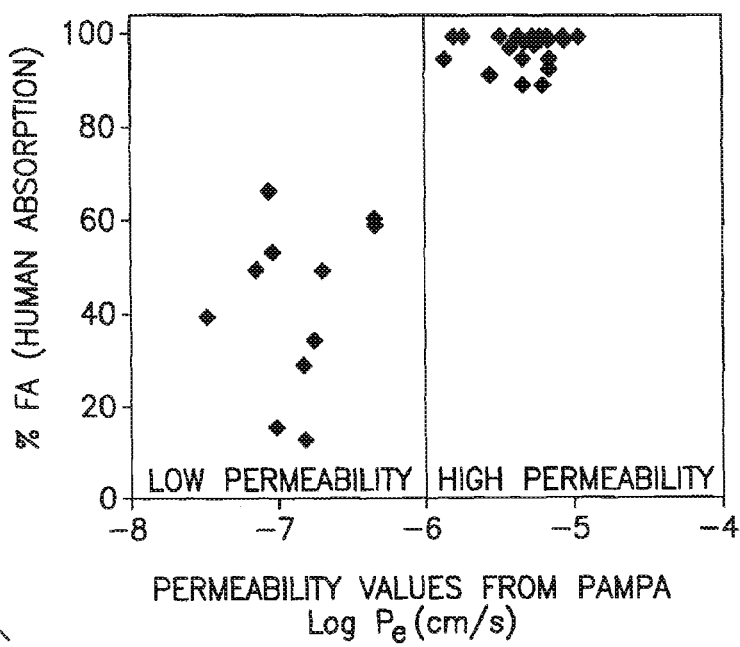
FIG.6

IMMOBILIZED MULTI-LAYER ARTIFICIAL MEMBRANE FOR PERMEABILITY MEASUREMENTS (PAMPA)

CROSS-REFERENCES TO RELATED APPLICATIONS

This application is a divisional application of U.S. application Ser. No. 11/552,606, filed Oct. 25, 2006, which claims priority to U.S. Provisional Patent Application No. 60/730,570, filed Oct. 27, 2005, the entire contents of which are incorporated by reference herein.

FIELD OF THE INVENTION

This invention relates to methods of preparing filter membranes and, more particularly, to methods of preparing filter membranes for drug permeability screening.

BACKGROUND OF THE INVENTION

Drug permeability screening has become a very important tool in the drug development process. Parallel Artificial Membrane Permeability Assay (PAMPA) has become a widely accepted high throughput drug permeability screening method.

In a typical PAMPA format, a pair of multi-well plates are used: a filter plate and a receiver plate. The filter plate includes open wells with a porous filter membrane extending across a bottom end of each well. The filter membrane is typically of polyvinylidine difluoride (PVDF) or a polycarbonate material. The receiver plate is a typical multi-well plate having closed bottom ends.

Referring to FIG. 1A, a conventional method used to prepare a filter membrane for PAMPA is shown. This prior method involves impregnating the membrane with an alkane solution of lipids. For example, as discussed in U.S. Published Application No. 2003/0219716 A1, published on Nov. 27, 2003, the alkane solution is typically a solution of phospholipids (e.g., 2% Dioleoyl-sn-glycero-3-phosphocholine (DOPC)) in dodecane. Once the filter membranes are prepared, buffered solutions containing the compounds being analyzed are disposed into the wells of the receiver plate. Buffered solutions without the analyzed compounds are disposed into the wells of the filter plate. The filter plate is placed atop the receiver plate with the filter membranes coming into contact with the buffered solutions of compounds disposed in the wells of the receiver plate. The concentrations of the compounds in the solutions of both the receiver plate and the filter plate are analyzed to observe the diffusion of the compounds through the filter membranes.

It has been found that, using prior art techniques, screening experiments must be conducted relatively soon after preparation of filter membranes for PAMPA because filter membranes impregnated with an alkane solution of lipids are unstable. For example, with reference to FIG. 1B, permeabilities measured by PAMPA using fresh prior art filter membranes (used immediately after preparation) and one-day old prior art filter membranes (stored at room temperature) are shown for seven different drug compounds. The filter membranes were impregnated with a 2% solution of phospholipids in dodecane. Significant variations in measured permeabilities were noted, with severe degradation in reliability with the lapse of relatively short periods of time (e.g., one day). Generally, the permeability results increased with time, indicating that the membranes degraded and became more permeable to all the compounds. As a result, filter membranes for PAMPA prepared with prior art techniques are not well-suited to be prepared in advance of testing and stored. The measurements were carried out with phosphate buffered saline (PBS) as the working buffer.

Therefore, there is a need in the art for stable, precoated filter membranes for PAMPA that can be prepared in advance of drug permeability screening and stored.

Furthermore, the permeability screening of drug candidates using the prior art is challenged by the incorrect prediction of a group of commercial compounds that are classified by the biopharmaceutical classification system (BCS) as high permeability compounds. Examples of these compounds include caffeine, antipyrine, ketoprofen, metoprolol, naproxen, phenytoin, timolol, and theophyline. The BCS defines highly permeable compounds as those that have human oral absorption greater than 90%. These compounds all have human oral absorption greater than 90%. However, the PAMPA permeability values found for these compounds by the prior art are low.

Therefore, there is a need in the art for improving the predictability of the permeability measurement for the currently under-predicted compounds.

Another challenge in the permeability screening of drug candidates using the prior art is from "sticky" compounds—compounds that are likely to bind to the plastic surface of the plate and/or be trapped inside the artificial membrane. "Sticky" compounds may have high mass retention (the percentage of the total mass of the compound lost during the permeability measurement as a result of binding to the plastic surface and/or retaining in the filter membrane). With high mass retention, it is difficult to obtain reliable, quantitative permeability results.

A further challenge in the permeability screening of drug candidates using the prior art is from low solubility compounds. Low solubility compounds precipitate when the dimethyl sulfoxide (DMSO) stock solution of the compound is diluted into the working buffer (usually PBS or other aqueous buffer). This results in difficulty in measuring the concentration of these compounds in the buffer and, therefore, the difficulty in obtaining reliable, quantitative permeability results.

Therefore, there is a need in the art for improving permeability measurements for "sticky" compounds and low solubility compounds.

SUMMARY OF THE INVENTION

With the subject invention, a method is provided for preparing a filter membrane including the steps of dispersing a liquid which is generally hydrophobic into the pores of a porous membrane, and applying a solution containing lipids onto at least a first surface of the porous membrane containing the liquid. Advantageously, the subject invention allows for filter membranes to be prepared which can be stored for periods of time without degradation in performance. The subject invention also has the following advantages: (1) it improves the correlation between test data and human absorption data thereby providing better predictions for in vivo permeability of test compounds; (2) it reduces the retention of "sticky" compounds inside the membrane, therefore improving the measurement of "sticky" compounds; and (3) the membrane retains its integrity when some organic solvents are added in the working buffer to increase the solubility of some compounds, therefore improving the ability to measure the permeability of low solubility compounds. The subject invention may have applicability in various contexts, but is well-suited for preparing filter membranes for permeability screening, particularly PAMPA.

The subject invention allows for filter membranes to be prepared which mimic the structure of a biological membrane. Specifically, the filter membrane of the subject invention may be prepared with a hydrophobic interior and hydrophilic surfaces.

These and other aspects of the subject invention will be better understood through a study of the following detailed description and accompanying drawings.

BRIEF DESCRIPTION OF THE FIGURES

FIG. 6 includes plots comparing human absorption and test data, specifically comparing PAMPA permeability values of thirty-eight drug compounds using filter membranes prepared in accordance with the subject invention and filter membranes prepared according to a prior art method versus human absorption.

DETAILED DESCRIPTION OF THE INVENTION

Figure 1A:
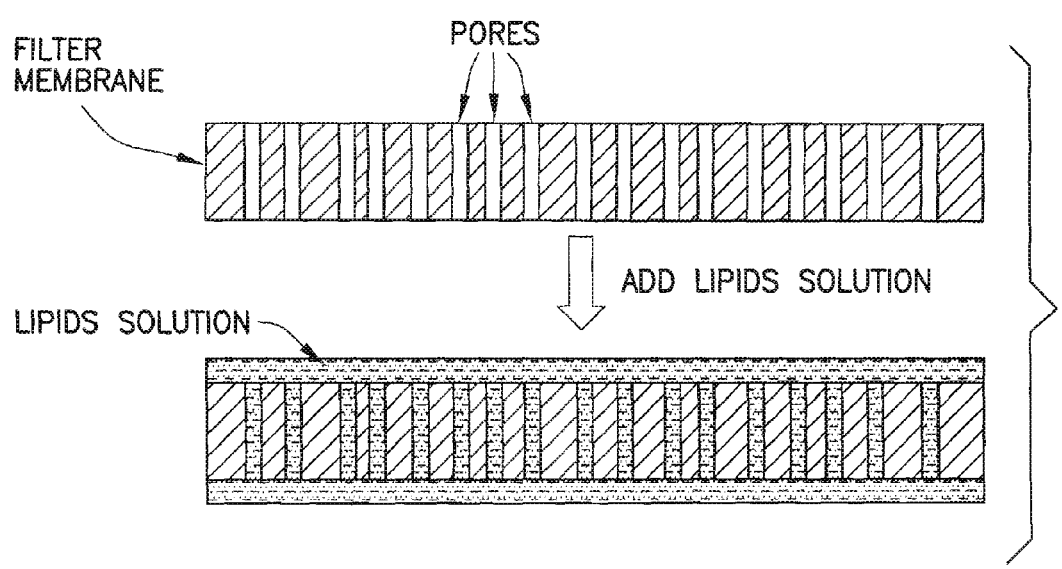
FIG. 1A is a flow chart showing a prior art method for impregnating a porous membrane with an alkane/lipids solution just prior to use.
Figure 1B:
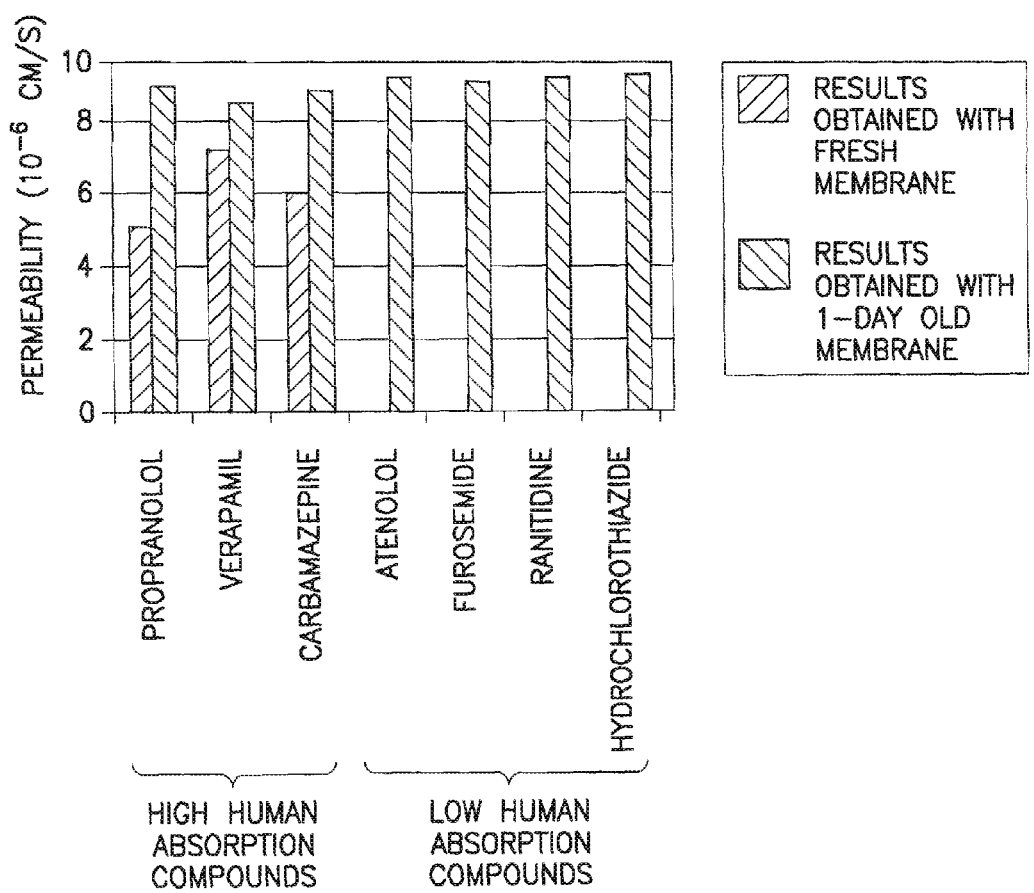
FIG. 1B is a chart showing permeability measurements of seven drug compounds with fresh and one-day old prior art filter membranes prepared according to the conventional method shown in FIG. 1A. The measurements were carried out using PBS as the working buffer.
Figure 2:
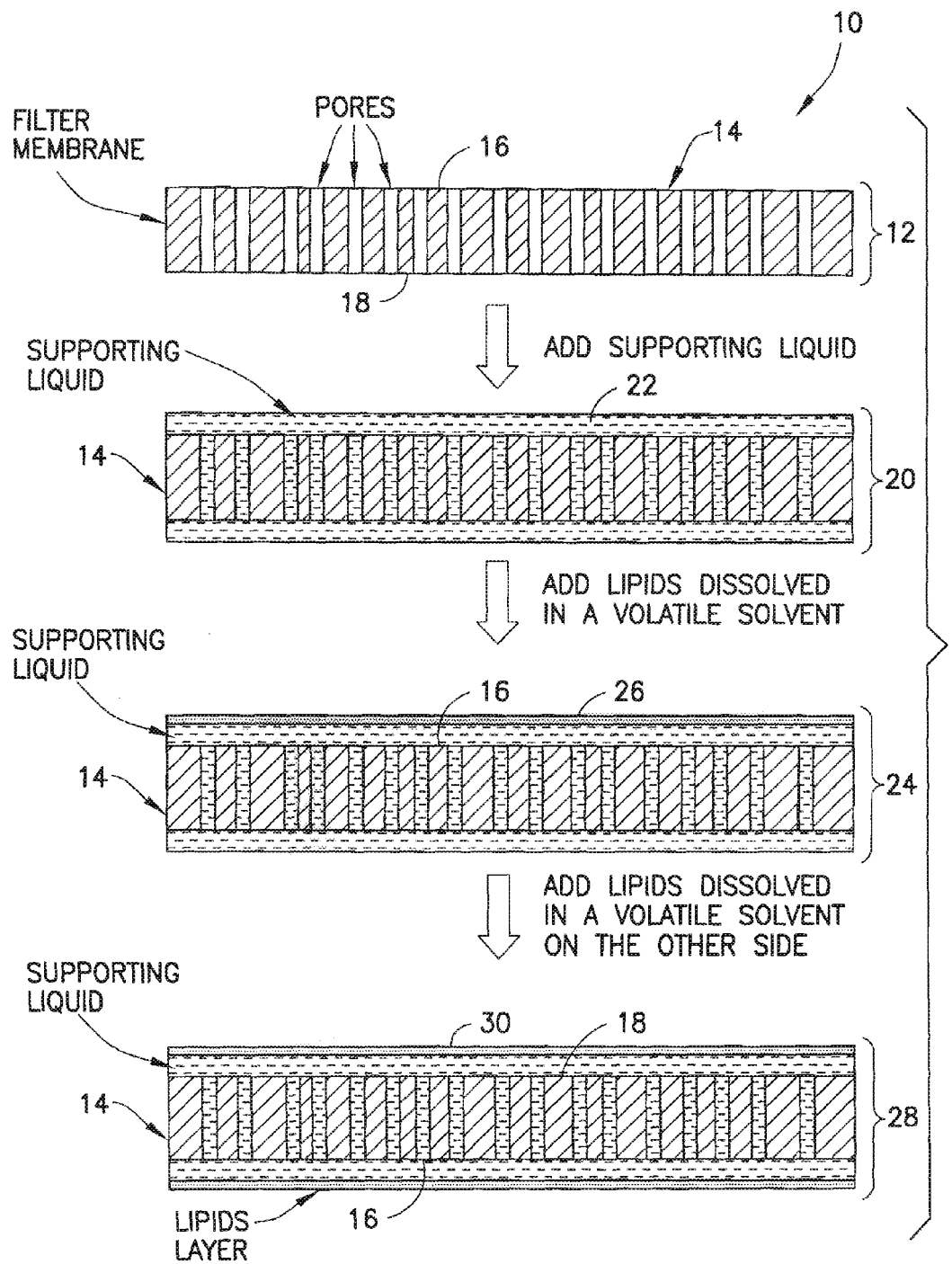
FIG. 2 is a flow chart showing preparation of a filter membrane in accordance with the subject invention. The geometry of the pores in the drawing is only illustrative and does not necessarily reflect the actual geometry of the pores in a porous membrane.
Figure 3:
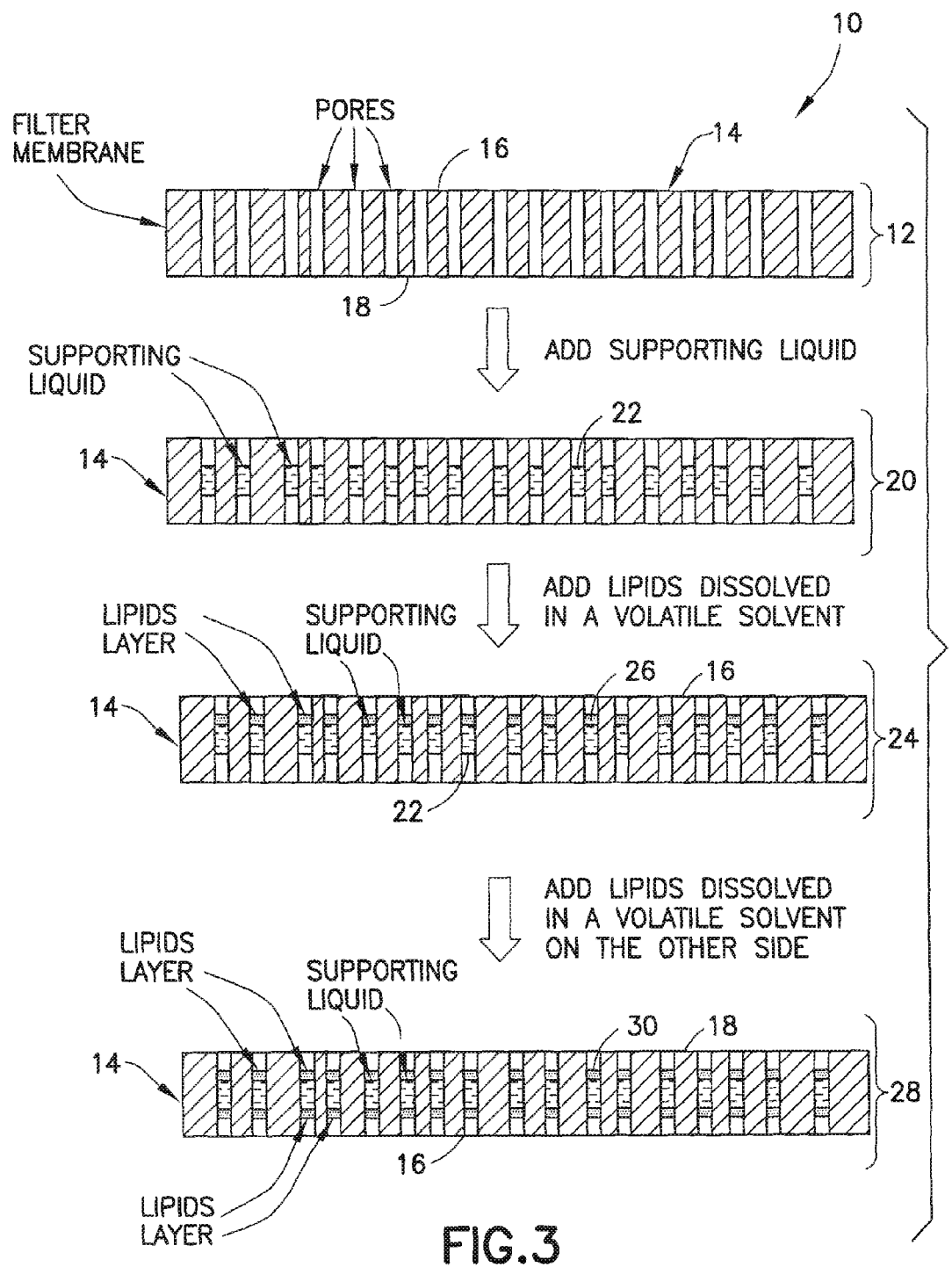
FIG. 3 is a flow chart showing preparation of a filter membrane in accordance with the subject invention. The geometry of the pores in the drawing is only illustrative and does not necessarily reflect the actual geometry of the pores in a porous membrane.

With reference to FIGS. 2 and 3, a method 10 is depicted of preparing a filter membrane. As will be appreciated by those skilled in the art, the resulting filter membrane may have applicability in various contexts, but is well-suited for permeability screening, particularly PAMPA.

In a first step 12, a porous membrane 14 is provided having spaced-apart first and second surfaces 16 and 18. The porous membrane 14 may be formed from any material compatible with its desired application (e.g., compatible with the liquids and solutions described below; compounds which are to be screened). By way of non-limiting example, the porous membrane 14 may be formed from PVDF or a polycarbonate material. In addition, it is preferred that the porous membrane 14 have pores in the range of 0.45-3.0 μm and a thickness in the range of 10-150 μm. The porous membrane 14 may be formed with generally constant thickness with the surfaces 16 and 18 being generally parallel. The pores in the porous membrane 14 may have various geometries and configurations. As further described below, the porous membrane 14 may be fixed to a sampling device, such as a filter plate.

In a second step 20 of the method 10, a supporting liquid 22 that is generally hydrophobic is dispersed into the pores of the porous membrane 14. The supporting liquid 22 can be dispersed into the pores using any known technique. Preferably, the supporting liquid 22 is generally lipophillic. The supporting liquid 22 is preferably an alkane having a carbon chain of more than twelve carbon atoms, such as hexadecane ($C_{16}H_{34}$). Other generally hydrophobic liquids can be used (e.g., various oils). The supporting liquid 22 is preferably substantially non-volatile.

Preferably, the supporting liquid 22 is dispersed into the pores of the porous membrane 14 using a solvent as a diluent. With this technique, it is preferred that the supporting liquid 22 be diluted in a solvent and then applied to the porous membrane 14. Alternatively, the supporting liquid 22 may be directly applied without being diluted (i.e., not in solution). The solvent may be of any type suitable for at least partially dissolving the supporting liquid 22. Preferably, the solvent is volatile, allowing for quick volatilization after application. It is further preferred that the solvent is an alkane having a short chain of carbon atoms, more preferably six or less carbon atoms, such as pentane ($C_5H_{12}$) or hexane ($C_6H_{14}$). Alcohol may also be a suitable solvent. For example, the supporting liquid 22 may be hexadecane and applied using hexane as a diluent, 10%-50% hexadecane in hexane.

As shown in FIG. 3, it is further preferred that the applied amount of the supporting liquid 22 be less than the collective volumes of the pores of the porous membrane 14 (i.e., the applied supporting liquid 22 does not fill up all of the pores of the porous membrane 14). If the supporting liquid 22 is applied in solution, the solution may be in an amount greater than the collective volumes of the pores of the porous membrane 14 where the volatilization of the solvent leaves the supporting liquid 22 in an amount less than the collective volumes of the pores of the porous membrane 14. The supporting liquid 22 can be applied in other amounts, such as in an amount equal to or greater than the collective volumes of the pores of the porous membrane 14, if desired. A biological membrane is typically about 10 nm thick and consists mainly of lipids. It is believed that reducing the amount of non-lipid components in the porous membrane 14 (i.e., reducing the amount of the supporting liquid 22) will result in a better model of a biological membrane.

As further shown in FIGS. 2 and 3, in a third step 24 of the method 10, a solution 26 is applied to the first surface 16 of the porous membrane 14. The solution 26 includes a solvent and lipids. The lipids are preferably amphiphilic constituents of biological membranes, such as phospholipids. The lipids may also be lipids extracted from a blood-brain barrier (e.g., brain polar lipid extracts) as disclosed in U.S. Pat. No. 7,060,428, the contents of which are incorporated by reference herein. The solvent may be of any type suitable for at least partially dissolving the lipids. Preferably, the solvent is volatile, allowing for quick volatilization after application. It is further preferred that the solvent is an alkane having a short chain of carbon atoms, more preferably six or less carbon atoms, such as pentane ($C_5H_{12}$) or hexane ($C_6H_{14}$). Alcohol may also be a suitable solvent. It is preferred that the solution 26 include a concentration in the range of 0.1%-10% of lipids. The solution 26 may also include non-lipid components of biological membranes.

Once the solution 26 is applied, the solvent volatilizes, leaving a lipid layer on the porous membrane 14. Depending on the applied amount of the supporting liquid 22, the lipid layer may be formed above, on, overlapping with, or below the first surface 16. With reference to FIG. 2, the lipid layer is shown above the first surface 16. With reference to FIG. 3, the lipid layer is shown below the first surface 16 (i.e., within the porous membrane 14). The location of the lipid layer will be at least partially dependent on the amount applied of the supporting liquid 22.

After step 24, and as shown by step 28 in FIGS. 2 and 3, a second solution 30 may optionally be applied to the second surface 18 of the porous membrane 14. It is preferred that the second solution 30 be applied to the second surface 18. The second solution 30 is prepared in the same manner as described above with respect to the solution 26. Preferably, the solutions 26 and 30 are the same solution, although different solvents, non-lipid components and/or lipids may be used for the solutions 26 and 30. Once the second solution 30 volatilizes, a lipid layer is formed on the porous membrane 14 in the same manner as discussed above with respect to the solution 26.

Figure 4:
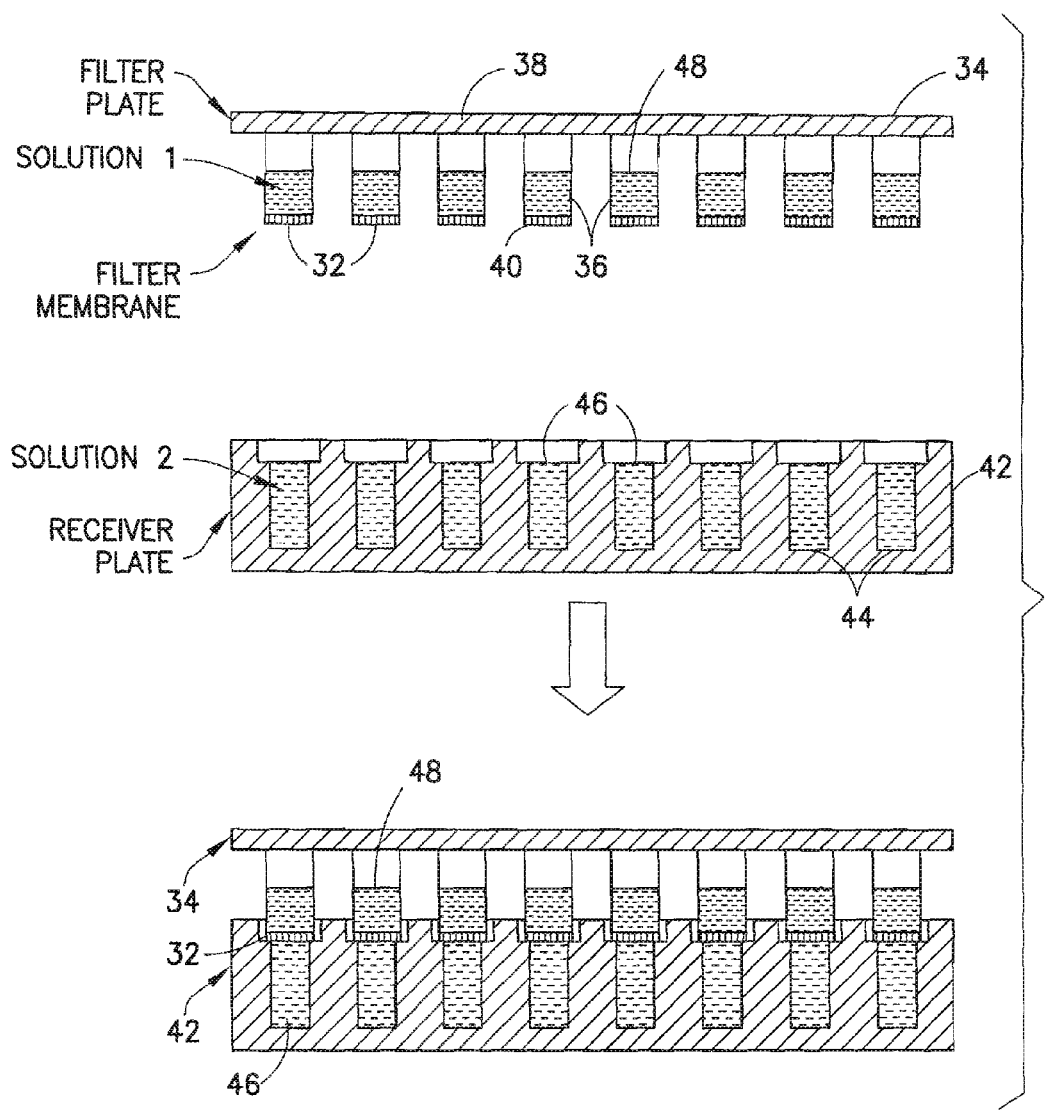
FIG. 4 is a schematic showing a PAMPA experiment using a filter membrane of the subject invention.

The method 10 results in the formation of a finished filter membrane 32 (FIG. 4). With the application of both the solutions 26 and 30, the filter membrane 32 mimics the structure of a biological membrane. Specifically, the resulting lipid layers on the filter membrane 32 provide hydrophilic surfaces, whereas the interior of the filter membrane 32 is hydrophobic, due to the presence of the supporting liquid 22. This is a similar characteristic arrangement to a cellular wall.

With reference to FIG. 4, the filter membrane 32 may be used in conjunction with a sampling device, preferably a filter plate 34. The filter plate 34 is formed in accordance with known configurations and includes one or more wells 36 having open top and bottom ends 38 and 40. One or more filter membranes 32 may be fixed across the open bottom ends 40 using any known technique, including fusion, bonding, mechanical interaction and combinations thereof. It is preferred that one of the filter membranes 32 be fixed to one of the open bottom ends 40. Preferably, the filter membranes 32 are attached to the filter plate 34 at the initial stage of the method 10 described above (i.e., the filter membrane 32 is attached during step 12 in an untreated state as the porous membrane 14). Although the filter membranes 32 may be attached to a sampling device after or during the method of preparation, it is preferred that disruption of the layers of the filter membranes 32 be minimized with attachment occurring before layer formation. The filter membranes 32 may be used with various sampling devices such as columns, test tubes, pipettes and the like.

Example

By way of exemplary illustration, the filter membrane 32 may be formed with: the porous membrane 14 being a PVDF membrane having a 0.45 µm pore size; the porous membrane 14 being fixed initially (before layer formation) to an open end of a well of a filter plate (e.g., a 96-well filter plate); hexadecane as the supporting liquid 22 (hexadecane may be applied using hexane as a diluent, 10%-50% hexadecane in hexane); hexane as the solvent in the solution 26 with phospholipids (1 mg/mL-5 mg/mL solution of phospholipids); and, the second solution 30 being used and being the same as the solution 26.

With reference to FIG. 4, an exemplary method of using the filter membrane 32 in permeability screening is depicted. Particularly, a PAMPA screening is shown. In addition to the filter plate 34, a receiver plate 42 is provided having a plurality of closed bottom wells 44 formed therein. Preferably, the number and locations of the wells 44 corresponds to the wells 36 of the filter plate 34. Buffer solutions 46 are disposed into the wells 44 including compounds that are to be screened. Buffer solutions 48 are disposed into the wells 36 above the filter membranes 32. The buffer solutions 48 do not include the compounds that are being screened. Once prepared, the filter plate 34 is placed atop the receiver plate 42 as shown in FIG. 4, with the filter membranes 32 coming into contact with the buffer solutions 46 disposed in the wells 44 of the receiver plate 42. With passage of time, compounds from the buffer solutions 46 migrate through the filter membranes 32 into the buffer solutions 48. The concentrations of the buffer solutions 46 and 48 are analyzed to evaluate the permeability of the relevant compound.

The buffer solutions 46, 48 may be solutions of PBS and methanol. In addition, the buffer solutions 46, 48 may include PBS with about 10%-20% methanol or acetonitrile.

In a conventional PAMPA format, 200-300 µl of the buffer solution 46 is required for each well of the receiver plate 42 so that when the filter plate 34 and the receiver plate 42 are coupled, the buffer solution 46 will be in full contact with the filter membrane 32. To reduce compound consumption, it is possible to employ a receiver plate where the bottoms of the wells 44 are raised, thereby reducing the volumes of the wells 44. This would reduce the required volume of the buffer solution 46 necessary to ensure full contact with the filter membrane 32, which would, thus, reduce compound consumption.

FIGS. 5-9 present various data relating to the subject invention. In FIGS. 5-9, reference to "subject invention membrane" is to a membrane formed according to the following details: a 96-well filter plate 34 was used having open bottom wells 36 with PVDF porous membranes 14 attached thereto; supporting liquid 22 of 1 µL hexadecane was dispersed into the pores of the PVDF porous membranes 14 by dispensing a 10 µL solution of 10% hexadecane in hexane onto the PVDF porous membranes 14; then lipid solution 26 of 5 µL solution of 4 mg/mL 1,2-dioleoyl-sn-glycero-3-phosphocholine (DOPC) in 0.4% ethanol, 99.6% hexane was dispensed onto one side of the PVDF porous membranes 14; then the filter plate 34 was flipped over and solution 30 of 5 µL solution of 4 mg/mL DOPC in 0.4% ethanol, 99.6% hexane was dispensed onto the opposing, bottom side of the PVDF porous membranes 14; and, after coating, the filter plate 34 was stored at −20° C.

Figure 7:
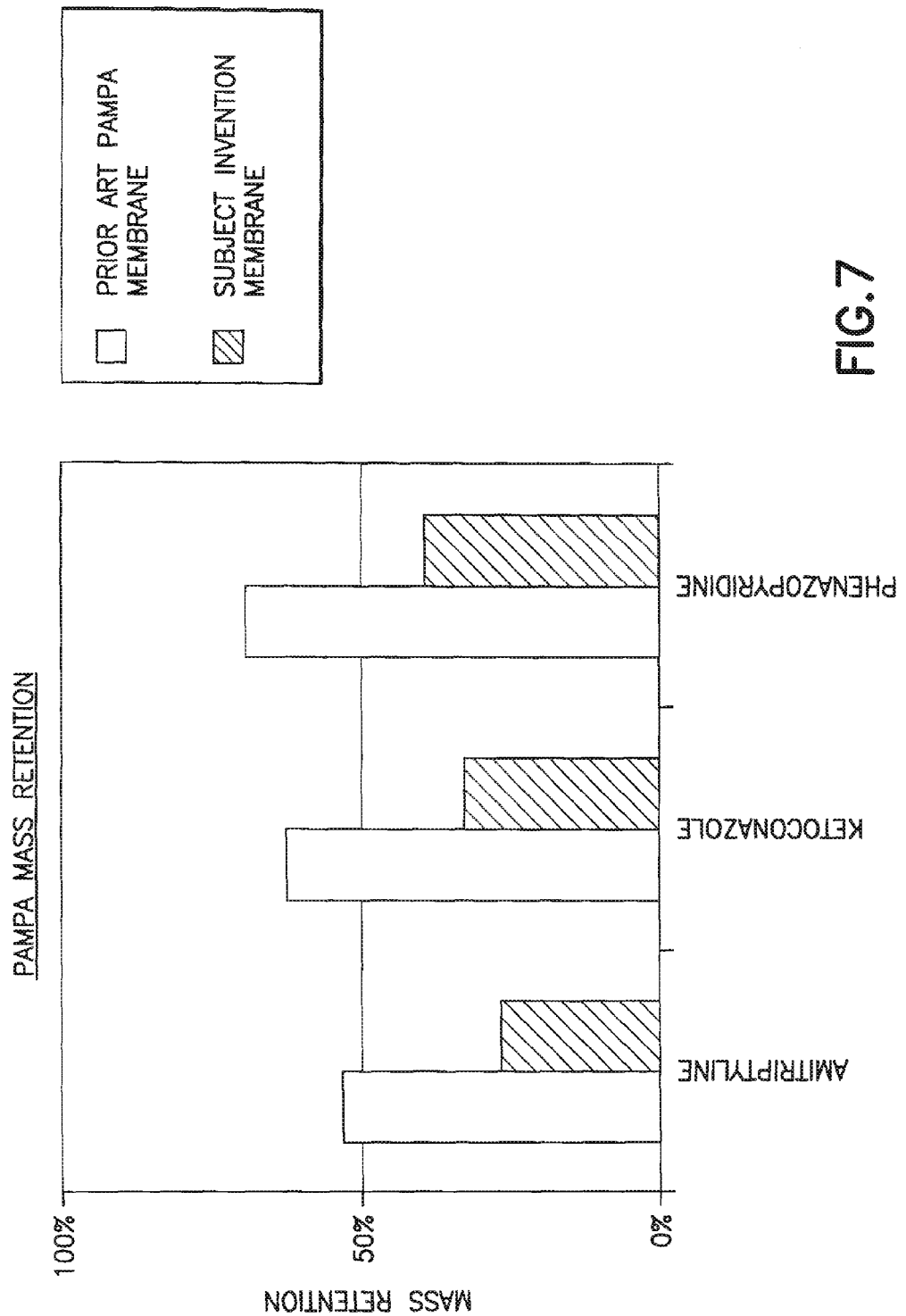
FIG. 7 is a graph showing mass retention of three "sticky" compounds in PAMPA using filter membranes prepared in accordance with the subject invention versus filter membranes prepared according to the prior art.
Figure 8:
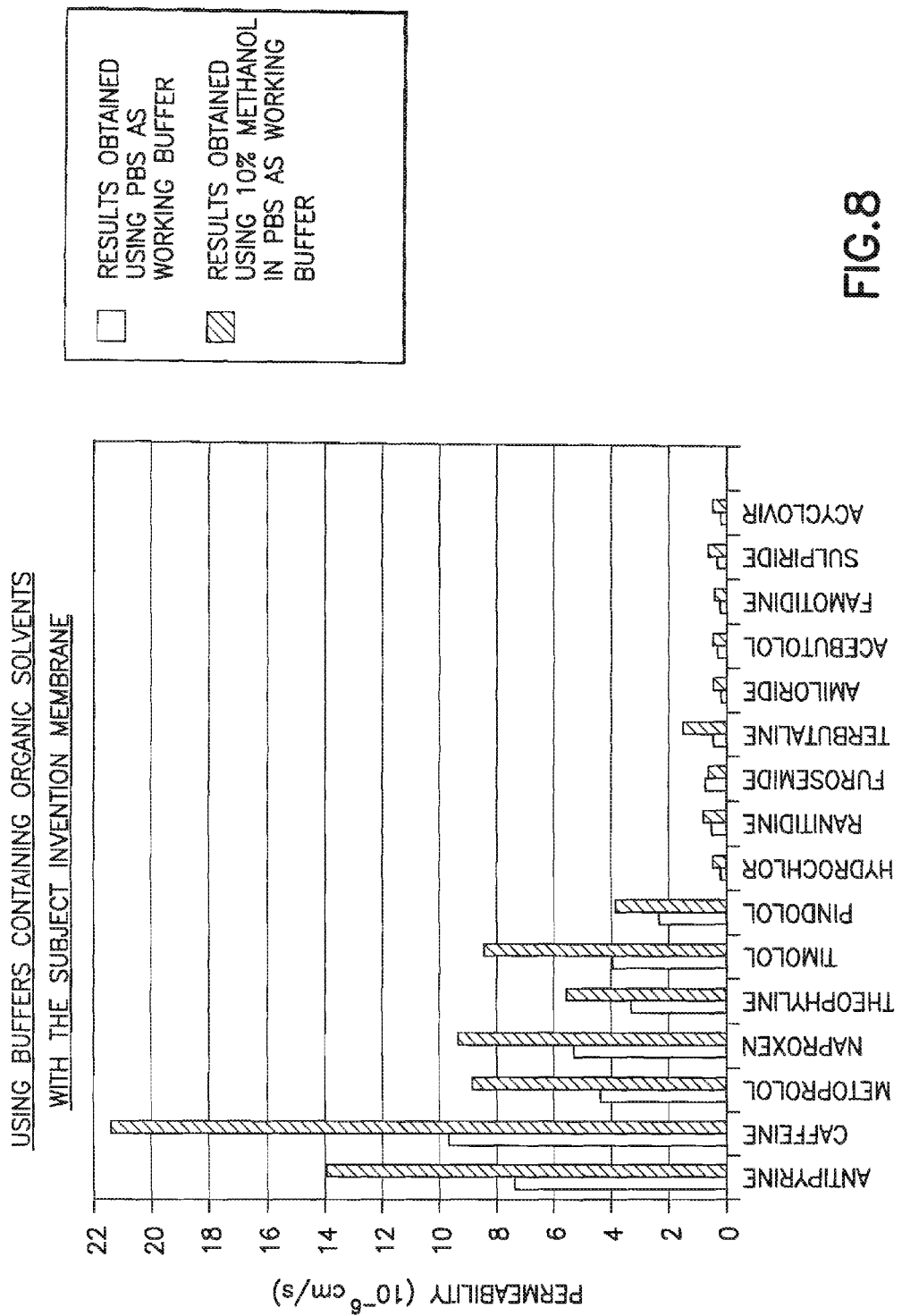
FIG. 8 is a graph showing permeability measurements of sixteen drug compounds using filter membranes of the subject invention. One group of measurements was carried out using PBS as the working buffer, while another group of measurements was carried out using 10% methanol, 90% PBS as the working buffer.

In addition, the PAMPA measurements of FIGS. 5-9 were carried out using PBS as the buffer solution 48 (except for a data set in FIG. 8, where 10% methanol, 90% PBS was used as the working buffer 48). The buffer solutions 46 containing compounds were prepared by diluting 10 mM DMSO stock solutions in the buffer solution 48 (final concentration of the buffer solution 46 was 200 µL/well).

The buffer solutions 46 including compounds were added to the wells 44 of the receiver plate 42 (300 μL/well) and the buffer solution 48 without compounds was added to the wells 36 of the filter plate 34 (200 μL/well). Then the filter plate 34 was coupled with the receiver plate 42 and the assembly was incubated in a humidity chamber without agitation at room temperature (except for a data set in FIG. 9, where the assembly was incubated in a humidity chamber without agitation at 37° C.) for 5 hours. At the end of the incubation, the plates 34, 42 were separated and 150 μL solution from each well 36, 44 of both the filter plate 34 and the receiver plate 42 was transferred to UV-transparent plates. The final concentrations of compounds in both donor wells and acceptor wells were analyzed by UV-plate reader. Permeability of the compounds were calculated using the formulae summarized below:

Permeability (in unit of cm/s):

$$P_e = \frac{-\ln[1 - C_A(t)/C_{equilibrium}]}{A*(1/V_D + 1/V_A)*t}$$

Mass Retention:

$$R = 1 - [C_D(t)*V_D + C_A(t)*V_A]/(C_0*V_D)$$

Where:
$C_0$=initial compound concentration in donor well (mM)
$C_D(t)$=compound concentration in donor well at time t. (mM)
$C_A(t)$=compound concentration in acceptor well at time t. (mM)
$V_D$=donor well volume=0.3 mL
$V_A$=acceptor well volume=0.2 mL $$C_{equilibrium} = [C_D(t)*V_D + C_A(t)*V_A]/(V_D + V_A)$$

A=filter area=0.3 cm$^2$
t=incubation time=18000 s (=5 hr)

Stability/Reproducibility of Subject Invention Membrane

Figure 5:
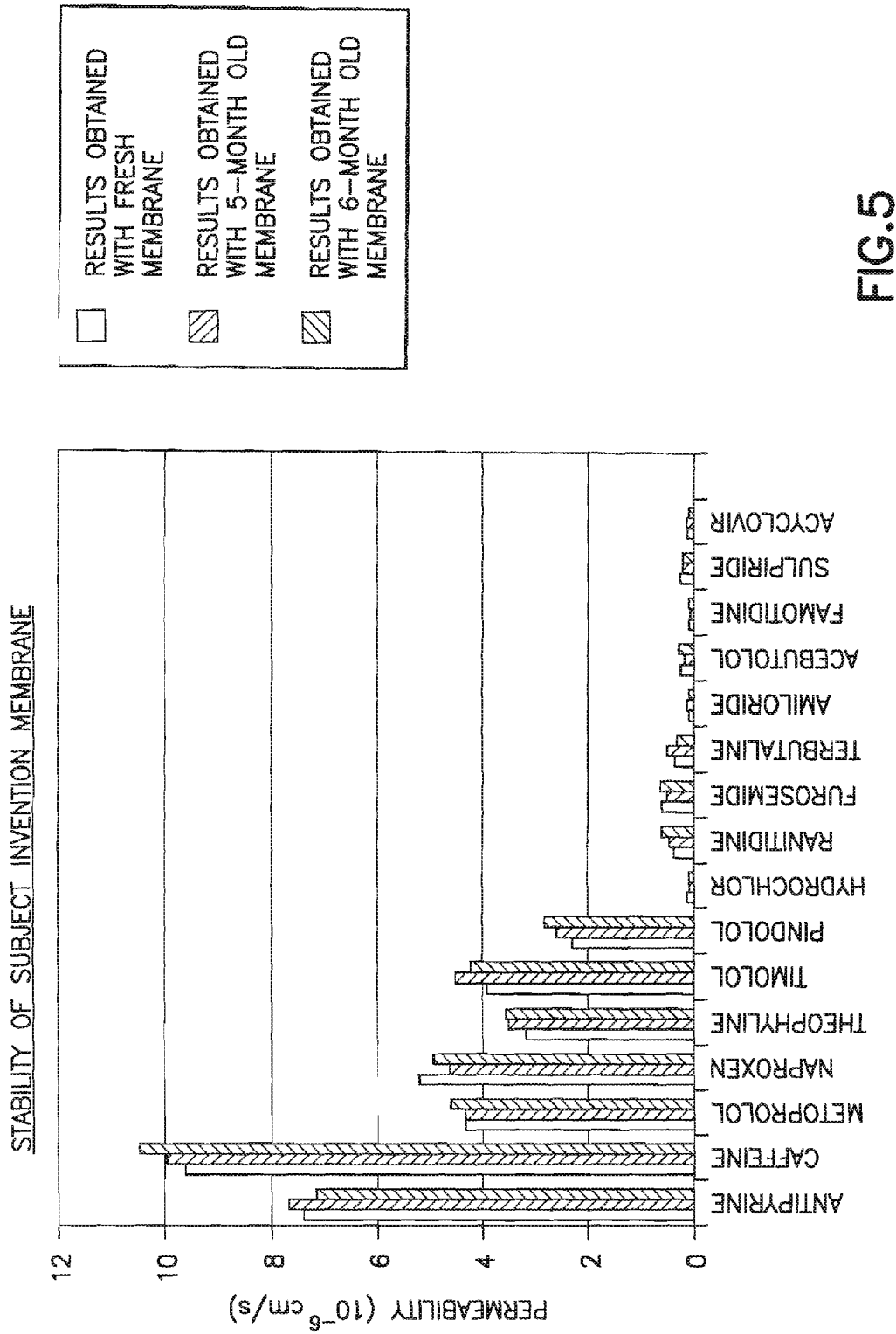
FIG. 5 is a graph showing permeability measurements of sixteen drug compounds with fresh, five-month old and six-month old filter membranes of the subject invention. The five-month old and six-month old filter membranes of the subject invention were stored at −20° C. prior to use.

With reference to FIG. 5, a graph is depicted showing the results of PAMPA screening using the subject invention membrane with respect to sixteen different drug compounds. As can be seen in FIG. 5, reproducible and consistent results using the method described above were obtained between freshly prepared, five-month old and six-month old filter membranes. The five-month old and six-month old filter membranes were stored at −20° C. prior to use. With the subject invention, the filter membranes may be made in advance of use and stored, without substantial degradation of performance.

Correlation of PAMPA Results with Human Absorption Data

FIG. 6 compares the performance of a prior art PAMPA membrane and the subject invention membrane by analyzing the correlation of obtained permeability data with human absorption data of thirty-eight compounds. The permeability data of the prior art PAMPA membrane were taken from literature [Ruell, J. A.; Avdeef, A.; Du, C.; Tsinman, K. "A Simple PAMPA Filter for Passively Absorbed Compounds", Poster, ACS National Meeting, Boston, August 2002]. The permeability data of the subject invention membrane were obtained using the method described above. In both sets of experiments, the working buffers were PBS, pH 7.4 and the assembly of the filter plate/receiver plate was incubated at room temperature without agitation. Because similar buffer and incubation conditions have been used, the significant differences in permeability data between the prior art and the subject invention membrane are due to differences in the prior art membrane and the subject invention membrane. Using the prior art PAMPA membrane, there is a group of compounds with high human absorption property that are under-predicted (circled in FIG. 6). Remarkably, these compounds are correctly predicted using the subject invention membrane.

The biopharmaceutical classification system (BCS) defines highly permeable compounds as those that have human oral absorption greater than 90%. Tables 1 and 2 list the compounds used in analyzing the correlation with human absorption in FIG. 6. In Table 1, twelve compounds with low BCS permeability are listed along with their human absorption data and permeability data reported for the prior art PAMPA membrane and obtained with the subject invention membrane. Both PAMPA membranes (prior art and the subject invention membrane) yielded permeability values lower than 1×10$^{-6}$ cm/s, therefore correctly predicting the low BCS permeabilities. In Table 2, sixteen compounds with high BCS permeability are listed along with their human absorption data and permeability data reported for the prior art PAMPA membrane and obtained with the subject invention membrane. The prior art PAMPA membrane yielded permeability values lower than 1×10$^{-6}$ cm/s for many compounds in this group, indicating poor predictability of actual human absorption. The subject invention membrane yielded permeability values for all the compounds in this group closer to actual human absorption, indicating significantly improved predictability.

TABLE 1

Low Human Absorption Compounds

| | | $P_e$ (10$^{-6}$ cm/s) | |
|---|---|---|---|
| Compound | Human Absorption | Prior Art Results | Subject Invention Membrane Results |
| sulphasalazine | 13% | 0.00 | 0.16 |
| acyclovir | 16% | 0.04 | 0.10 |
| nadolol | 30% | 0.28 | 0.16 |
| sulpiride | 35% | 0.03 | 0.18 |
| famotidine | 40% | 0.06 | 0.04 |
| acebutolol | 50% | 0.03 | 0.21 |
| amiloride | 50% | 0.00 | 0.08 |
| atenolol | 54% | 0.06 | 0.10 |
| terbutaline | 60% | 0.05 | 0.46 |
| furosemide | 61% | 0.01 | 0.46 |
| ranitidine | 61% | 0.01 | 0.45 |
| hydrochlorothiazide | 67% | 0.02 | 0.09 |

TABLE 2

High Human Absorption Compounds

| | | $P_e$ (10$^{-6}$ cm/s) | |
|---|---|---|---|
| Compound | Human Absorption | Prior Art Results | Subject Invention Membrane Results |
| phenytoin | 90% | 0.38 | 5.73 |
| timolol | 90% | 0.61 | 4.45 |
| pindolol | 92% | 0.12 | 2.64 |
| ibuprofen | 95% | 2.4 | 4.39 |
| metoprolol | 95% | 0.41 | 4.29 |
| theophyline | 98% | 0.04 | 3.53 |
| warfarin | 98% | 1.58 | 5.28 |
| diclofenac | 99% | 1.37 | 6.30 |
| naproxen | 99% | 0.34 | 4.65 |
| antipyrine | 100% | 0.74 | 7.51 |
| caffeine | 100% | 1.2 | 9.89 |
| carbamazepine | 100% | 6.4 | 7.79 |

TABLE 2-continued

High Human Absorption Compounds

| Compound | Human Absorption | $P_e$ ($10^{-6}$ cm/s) Prior Art Results | Subject Invention Membrane Results |
|---|---|---|---|
| clonidine | 100% | 1.5 | 4.92 |
| indomethacin | 100% | 0.3 | 6.24 |
| ketoprofen | 100% | 0.05 | 3.10 |
| piroxicam | 100% | 2.64 | 4.02 |

Mass Retention Improvements

With reference to FIG. 7, a graph is depicted which shows mass retention of three "sticky" compounds. Mass retention is defined as the percentage of the total mass of the compound lost during the permeability measurement as a result of binding to the plastic surface and/or retaining in the filter membrane. The mass retention values of the three listed compounds using a prior art PAMPA membrane were reported in literature [Avdeef, A.; Strafford, M.; Block, E.; Balogh, M.; Chambliss, W.; Khan, I. "Drug Absorption in vitro Model: Filter-Immobilized Artificial Membranes 2. Studies of the Permeability Properties of Lactones in piper Methysticum Forst", Eur. J. Pharm. Sci. Vol. 14, Page 271 (2001)]. As can be seen from FIG. 7, using the subject invention membrane formed and tested in accordance with the details set forth above, mass retention of the compounds is reduced compared to a prior art PAMPA membrane. This is most likely due to the reduced solvent amount of the subject invention membrane compared to the prior art membrane. It is believed that the excess solvents in the prior art membrane may act like a trap for the "sticky" compounds.

The mass retention of some "sticky" compounds is further reduced when polypropylene plates are used instead of conventional polystyrene plates. This suggests that some of the mass retentions are due to the compounds sticking to the polystyrene surface. Therefore, in some preferred embodiments, the filter plate 34 and/or the receiver plate 42 is made from polypropylene to reduce the mass retention contributed by compounds sticking to polystyrene surface. However, conventional polystyrene plates may alternatively be used.

Using Organic Solvent in the Working Buffer for Low Solubility Compounds

With reference to FIG. 8, a graph is depicted comparing the results of PAMPA screening using PBS as the working buffer and using 10% methanol, 90% PBS as the working buffer. The filter membranes which were used were formed and tested according to the details set forth above. As can be seen in FIG. 8, the measured permeability of all the compounds increases with the use of 10% methanol, while the measured permeability for high permeability compounds has greater increases than the increases for measured permeability of low permeability compounds. As a result, the prediction for high and low permeability remains unchanged relative to the relevant buffer (PAMPA is primarily used for ranking compounds as high or low permeability). Therefore, the filter membranes retained their integrity and produced consistent results when 10% methanol was added in the working buffer. It has been found that many low solubility compounds have significantly increased solubility when 10% methanol is used in the working buffer. For example, it has been reported [Liu H.; Sabus, C.; Carter, G. T.; Du, C.; Avdeef, A.; Tischler, M. "In Vitro Permeability of Poorly Aqueous Soluble Compounds Using Different Solubilizers in the PAMPA Assay with Liquid Chromatography/Mass Spectrometry Detection", Pharmaceutical Research, Vol. 20, Page 1820 (2003)] that the permeability of miconazole and terfenadine, both having low solubility, are difficult to measure using the conventional prior art PAMPA method. Using the filter membrane of the current invention and using 10% methanol in the working buffer, the permeability of miconazole and terfenadine can be measured along with other test compounds. Therefore, in some preferred embodiments, the permeability measurement is carried out using 10% methanol in the working buffer.

Performing Permeability Assay at 37° C.

Figure 9:
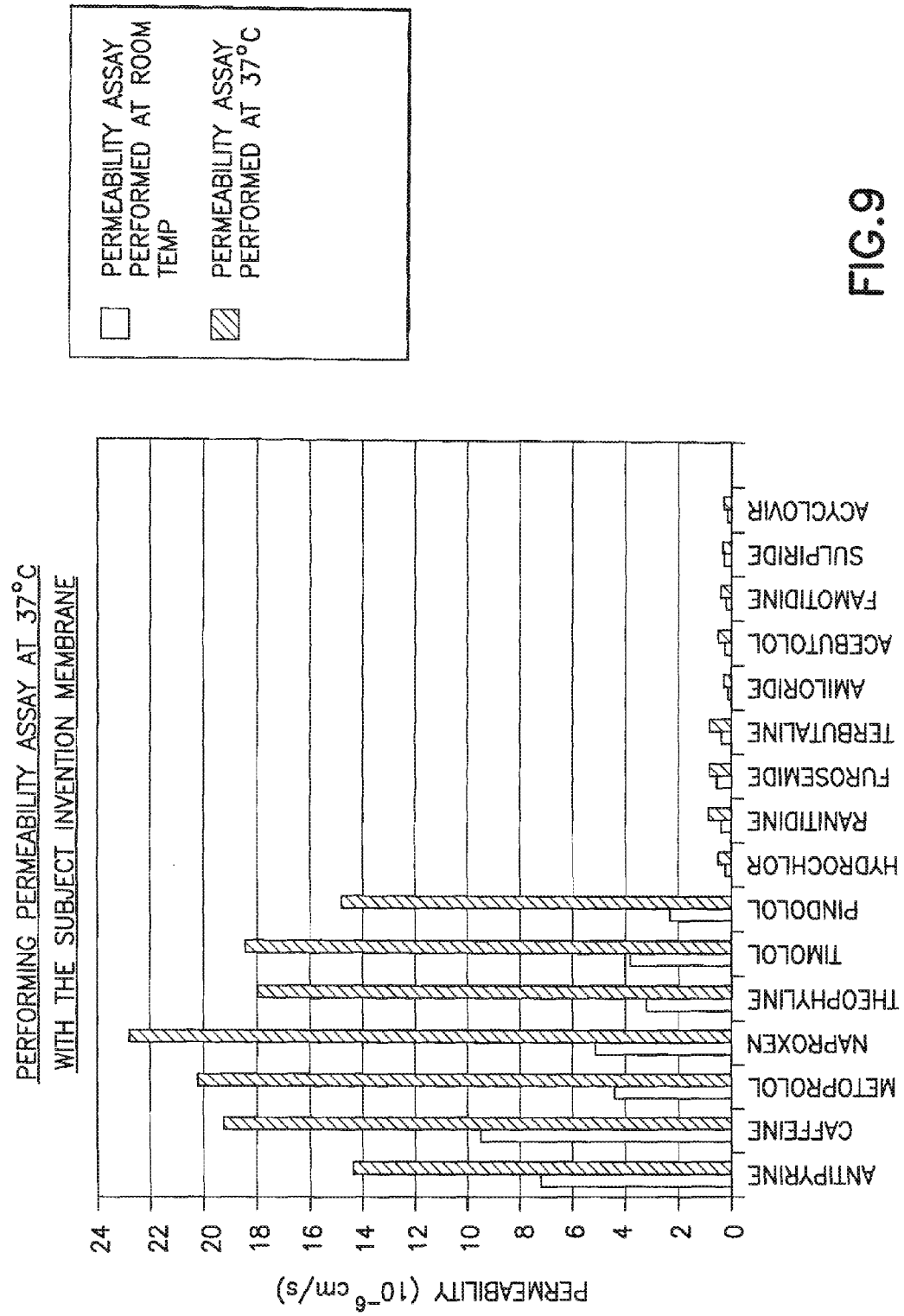
FIG. 9 is a graph showing permeability measurements of sixteen drug compounds using filter membranes of the subject invention. One group of measurements was carried out in a humidity chamber at room temperature, while another group of measurements was carried out in a humidity chamber at 37° C.

With reference to FIG. 9, a graph is depicted comparing the results of PAMPA screening with the subject invention membrane performed at room temperature and performed at 37° C. The filter membranes which were used were formed and tested according to the details set forth above. As can be seen in FIG. 9, the permeability of all the listed compounds increases when the assay is performed at 37° C., while the measured permeabilities for high permeability compounds has greater increases than the increases for measured permeability of low permeability compounds. As a result, the prediction for high and low permeability remains unchanged relative to the temperature. The filter membranes retained their integrity and produced consistent results when the assay is performed at 37° C. The use of 37° C. may provide more information regarding the drug transport at physiological temperature.

What is claimed is:

1. A porous filter membrane prepared by a method comprising:
   dispersing a hydrophobic liquid into pores of a porous filter membrane having a first and second surface to form a hydrophobic liquid layer therein, wherein the hydrophobic liquid layer consists of a substantially non-volatile alkane; and
   applying a solution containing lipids onto the first surface of the porous filter membrane containing the hydrophobic liquid to form a first lipid layer extending across the first surface; applying the solution containing lipids onto the second surface of the porous filter membrane so as to form a second lipid layer on the second surface; wherein the pores of the porous membrane have a collective volume, wherein the resulting porous filter membrane comprises the hydrophobic liquid layer located between the first and second lipid-containing layers, wherein the hydrophobic liquid layer comprises a continuous layer across at least one of the pores, and wherein a volume of the hydrophobic liquid layer in the porous filter membrane is less than the collective volume of the pores of the porous filter membrane.

2. The porous filter membrane of claim 1, wherein the first and second surfaces are parallel.

3. The porous filter membrane of claim 1, wherein the lipids of the solution comprise amphiphilic constituents of biological membranes.

4. The porous filter membrane of claim 1, wherein the lipids of the solution comprise phospholipids.

5. The porous filter membrane of claim 1, wherein the lipids of the solution comprise components derived from a blood-brain barrier.

6. The porous filter membrane of claim 1, wherein the solution contains non-lipid components of biological membranes.

7. The porous filter membrane of claim 1, wherein the substantially non-volatile alkane is hexadecane.

8. The porous filter of claim 1, wherein the substantially non-volatile alkane comprises a chain of more than twelve carbon atoms.

9. The porous filter membrane of claim 1, wherein the solution consists of a volatile solvent and the lipids, and wherein the lipids of the solution are at least partially dissolved in the volatile solvent.

10. The porous filter membrane of claim 9, wherein the volatile solvent includes hexane.

11. The porous filter membrane of claim 9, wherein the volatile solvent comprises pentane.

12. The porous filter membrane of claim 9, wherein the volatile solvent comprises an alkane having a chain of six or less carbon atoms.

13. The porous filter membrane of claim 9, wherein the volatile solvent comprises an alkane having a chain of six or less carbon atoms and an alcohol.

14. The porous filter membrane of claim 1, wherein the porous filter membrane comprises polyvinylidine difluoride.

15. The porous filter membrane of claim 1, wherein the porous filter membrane comprises polycarbonate.

16. The porous filter membrane of claim 1, wherein the hydrophobic liquid is dispersed into the porous filter membrane by:
    diluting a base hydrophobic liquid in a volatile solvent to form the hydrophobic liquid;
    applying the hydrophobic liquid to the porous filter membrane; and
    allowing the volatile solvent to volatilize.

17. A filter membrane comprising:
    a porous filter membrane comprising a first surface and a second surface;
    a layer of hydrophobic liquid dispersed within pores of the porous filter membrane,
        wherein the hydrophobic liquid consists of a substantially non-volatile alkane;
    a first lipid-containing layer supported by the first surface of the porous filter membrane; and
    a second lipid-containing layer supported by the second surface of the porous filter membrane,
    wherein the layer of hydrophobic liquid is located between the first and second lipid-containing layers,
    wherein the layer of hydrophobic liquid comprises a continuous layer across at least one of the pores, and
    wherein a volume of the layer of hydrophobic liquid dispersed within the pores is less than a collective volume of the pores of the porous filter.

18. The filter membrane of claim 17, wherein the first lipid-containing layer comprises amphiphilic constituents of biological membranes.

19. The filter membrane of claim 17, wherein the first lipid-containing layer comprises phospholipids.

20. The filter membrane of claim 17, wherein the first lipid-containing layer comprises components derived from a blood-brain barrier.

21. The filter membrane of claim 18, wherein the second lipid-containing layer comprises phospholipids.

22. The filter membrane of claim 18, wherein the second lipid-containing layer comprises components derived from a blood-brain barrier.

23. The filter membrane of claim 19, wherein the second lipid-containing layer comprises amphiphilic constituents of biological membranes.

24. The filter membrane of claim 19, wherein the second lipid-containing layer comprises components derived from a blood-brain barrier.

25. The filter membrane of claim 20, wherein the second lipid-containing layer comprises amphiphilic constituents of biological membranes.

26. The filter membrane of claim 20, wherein the second lipid-containing layer comprises phospholipids.

27. The filter membrane of claim 17, wherein the substantially non-volatile alkane is hexadecane.

28. The filter membrane of claim 17, wherein the substantially non-volatile alkane comprises a chain of more than twelve carbon atoms.

29. The filter membrane of claim 17, wherein the porous filter membrane comprises polyvinylidine difluoride.

30. The filter membrane of claim 17, wherein the porous filter membrane comprises polycarbonate.

31. The porous filter membrane of claim 1, wherein the first and second lipid-containing layers are supported by the resulting hydrophobic liquid layer.

32. The filter membrane of claim 17, wherein the first and second lipid-containing layers are supported by the resulting hydrophobic liquid layer.

33. The porous filter membrane of claim 1, wherein:
    an interior of the porous filter membrane is hydrophobic, and
    the first lipid layer and the second lipid layer are hydrophilic.

34. The porous filter membrane of claim 1, wherein:
    the substantially non-volatile alkane is hexadecane,
    the solution consists of a volatile solvent and the lipids, and
    the volatile solvent comprises ethanol and hexane.

35. The filter membrane of claim 17, wherein the filter membrane is stable following storage for five-months.

* * * * *

UNITED STATES PATENT AND TRADEMARK OFFICE
CERTIFICATE OF CORRECTION

PATENT NO. : 9,999,859 B2
APPLICATION NO. : 14/613774
DATED : June 19, 2018
INVENTOR(S) : Xiaoxi Kevin Chen et al.

Page 1 of 1

It is certified that error appears in the above-identified patent and that said Letters Patent is hereby corrected as shown below:

On the Title Page

On page 2, Column 2, item (56), other publications, Line 12, delete ""Physicochecmical" and insert -- "Physicochemical --, therefor.

On page 2, Column 2, item (56), other publications, Line 31, delete ""Predicition" and insert -- "Prediction --, therefor.

On page 2, Column 2, item (56), other publications, Line 45, delete "Applications." and insert -- Applications; --, therefor.

In the Claims

In Column 11, Line 1, Claim 8, delete "porous filter" and insert -- porous filter membrane --, therefor.

Signed and Sealed this
Nineteenth Day of November, 2019

Andrei Iancu
*Director of the United States Patent and Trademark Office*